United States Patent [19]

Nussbaumer et al.

[11] Patent Number: 5,488,135
[45] Date of Patent: Jan. 30, 1996

[54] BIS(PHENYL)ETHANE DERIVATIVES

[75] Inventors: Peter Nussbaumer, Maria Enzersdorf; Anton Stutz, Vienna, both of Austria

[73] Assignee: Sandoz Ltd., Switzerland

[21] Appl. No.: 962,370

[22] Filed: Oct. 16, 1992

[30] Foreign Application Priority Data

Oct. 16, 1991 [AT] Austria .................... 9121943

[51] Int. Cl.⁶ .................... C07C 69/76; A01N 37/10
[52] U.S. Cl. .................... 560/266; 560/67
[58] Field of Search .................... 560/66, 67, 71; 514/544

[56] References Cited

U.S. PATENT DOCUMENTS 3,657,430  4/1972  Shen et al. .................... 424/230

FOREIGN PATENT DOCUMENTS

| | | |
|---|---|---|
| 28305 | 5/1981 | European Pat. Off. . |
| 269619 | 7/1989 | Germany . |
| 293108 | 8/1991 | Germany . |
| 92/0721 | 8/1992 | South Africa . |
| 88/03800 | 6/1988 | WIPO . |
| 88/03806 | 6/1988 | WIPO . |
| 92/20642 | 11/1992 | WIPO . |

*Primary Examiner*—Paul J. Killos
*Attorney, Agent, or Firm*—Robert S. Honor; Melvyn M. Kassenoff; Joseph J. Borovian

[57] ABSTRACT

The invention concerns the compounds of formula I

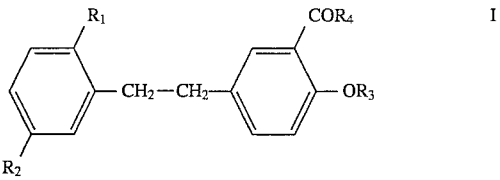

wherein the substituents have various significances, in free form and, where such forms exist, in salt form. The compounds have potent antihyperproliferative/antiinflammatory and anticancer activity.

8 Claims, No Drawings

BIS(PHENYL)ETHANE DERIVATIVES

The invention relates to the field of bis(phenyl)ethane derivatives. It concerns the compounds of formula I

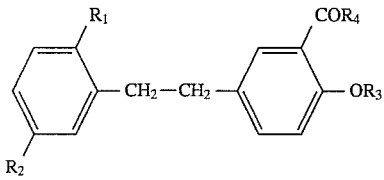

wherein $R_1$ and $R_2$ independently are alkoxy, $R_3$ is hydrogen or acyl, and $R_4$ is alkoxy, in free form and, where such forms exist, in salt form, hereinafter briefly named "the compounds of the invention".

The compounds of the invention possess differentiated pharmacological, in particular antihyperproliferative and antitumor activity.

Alkyl as part of a substituent such as alkoxy preferably is of 1 to 4 carbon atoms; it particularly is methyl or ethyl.

Acyl preferably is the residue of a carboxylic acid, in particular an alkyl, arylalkyl or aryl carboxylic acid, whereby aryl preferably is phenyl, and the alkylene part of acyl, including the carbonyl group, preferably is of 1 to 5 carbon atoms. A preferred acyl moiety is acetyl.

In a preferred group of compounds of the invention $R_1$ and $R_2$ independently are alkoxy of 1 to 4 carbon atoms, and $R_3$ and $R_4$ are as defined above.

In a further subgroup $R_1$ and $R_2$ independently are alkoxy of 1 to 4 carbon atoms, $R_3$ is hydrogen or alkylcarbonyl of altogether 2 to 5 carbon atoms, and $R_4$ is alkoxy of 1 to 4 carbon atoms (compounds Is); $R_1$ and $R_2$ therein especially are independently methoxy or ethoxy; and $R_4$ therein especially is methoxy or ethoxy.

The compounds of the invention may be prepared by a process which comprises a) reducing a corresponding compound of formula II

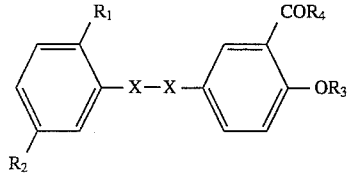

wherein —X—X— is vinylene or ethinylene, or b) esterifying or acylating a compound of formula III

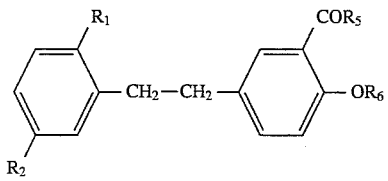

wherein $R_1$, $R_2$, $R_3$ and $R_4$ are as defined above, $R_5$ is hydroxy or alkoxy and $R_6$ is hydrogen or acyl, and optionally converting by transesterification an alkoxy group $R_4$ into a different alkoxy group $R_4$, whereby functional groups may be in protected form and the protecting groups removed after reaction has taken place, and recovering the resultant compounds of formula I in free form or, where such forms exist, in salt form.

The process of the invention can be effected in conventional manner.

Process variant a) conveniently is effected by hydrogenation. Preferably hydrogen is used together with a hydrogenation catalyst such as Pd, Pt or Rh, more preferably Pd on charcoal.

Process variant b) is also effected in conventional manner.

Transesterification (as well as esterification) preferably is effected by reaction in the presence of a strong acid such as sulfuric acid with the alcohol corresponding to the ester group which it is desired to introduce.

Removal of protecting groups is also effected in conventional manner. A functional group which may be suitably protected is hydroxy, protected by e.g. trialkylsilyl. The removal of e.g. trialkylsilyl may be effected by treatment with hydrofluoric acid in a solvent such as acetonitrile.

The resultant compounds of the invention can be isolated from the reaction mixture and purfied according to known methods, e.g. chromatographically.

The starting materials can also be obtained in conventional manner:

The compounds of formula II wherein —X—X— is vinylene may be prepared by reacting a corresponding compound of formula IV

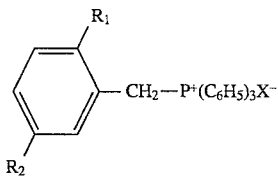

wherein $X^-$ is an anion, preferably bromide, with a corresponding compound of formula V

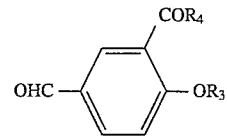

in a manner conventional for Wittig/Horner/Emmons-type reactions, by treatment of the phosphorous component with a base, such as an alkyllithium, an alkali hydride or an alkali amide, e.g. sodium amide, lithium diisopropylamide, or an alkali alcoholate, at a temperature between about −70° and about 100° C. and simultaneous or subsequent conversion with the carbonyl component at temperatures between about −70° and about 120° C., preferably about −60° to 60° C., in appropriate solvents, such as, for example, tetrahydrofuran, toluene or dimethylsulfoxide.

The compounds of formula II wherein —X—X— is ethinylene may be prepared by reacting a corresponding compound of formula VI

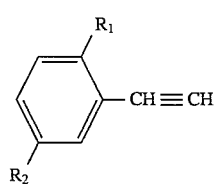

with a corresponding compound of formula VII

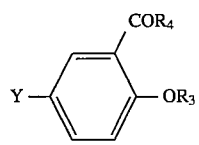

wherein Y is halogen, preferably iodine,
following standard procedures for the Heck reaction of haloolefins with acetylenes.

The compounds of formula III wherein $R_6$ is hydrogen, and the compounds of formula III wherein $R_5$ is hydroxy can be prepared analogously as described above or by deacylation or dealkylation of corresponding compounds of formula I wherein $R_3$ is acyl and/or $R_4$ is alkoxy.

Insofar as their preparation is not specifically described herein, starting materials are known or can be prepared according to known methods or analogously to known methods or to the methods described in the Examples.

In the following illustrative Examples all temperatures are in degrees Centigrade; all NMRs are $^1$H-NMRs (CDCl$_3$):

EXAMPLE 1

5-[2-(2,5-Dimethoxyphenyl)ethyl]-2-hydroxybenzoic acid methyl ester

[Formula I: $R_1$, $R_2$, $R_4$=OCH$_3$; $R_3$=H]
[Process Variant a)]

60 mg of 5-[2-(2,5-dimethoxyphenyl)ethinyl]-2-hydroxybenzoic acid methyl ester or 60 mg of an E/Z mixture of 5-[2-(2,5-dimethoxyphenyl)ethenyl] -2-hydroxybenzoic acid methyl ester are dissolved in 10 ml of ethyl acetate. After addition of 10 mg of 10% Pd/C the mixture is stirred overnight under an atmosphere of hydrogen, filtered over Celite® and evaporated to dryness under reduced pressure. The title compound is obtained [colorless crystals; M.P. 65° after chromatographic purification; M.P. 67° (from ethanol)].

The starting materials are obtained as follows:

Under argon atmosphere 240 mg of 2,5-dimethoxyphenylacetylene and 493 mg of methyl 5-iodosalicylate are dissolved in 20 ml of oxygen-free and dry benzene. The mixture is treated with 85 mg of tetrakis (triphenylphosphine)palladium, 20 mg of copper(I)iodide and 450 mg of triethylamine, stirred at room temperature overnight and then poured onto 100 ml of aqueous pH 7 buffer. After extraction with ethyl acetate and purification by chromatography on silicagel, 5-[2-(2,5-dimethoxyphenyl)ethinyl]-2-hydroxybenzoic acid methyl ester is obtained (colorless crystals of M.P. 105°–108°).

6.6 mmol of lithium diisopropylamide in tetrahydrofuran/n-hexane are added at −40° to a suspension of 1 g of 2,5-dimethoxybenzyl-triphenylphosphonium bromide in 15 ml of absolute tetrahydrofuran. After stirring for one hour the mixture is cooled to −70° and treated slowly with 372 mg of 3-methoxycarbonyl-4-hydroxybenzaldehyde dissolved in 5 ml of absolute tetrahydrofuran. The mixture is stirred for one hour at −70° and for two hours at room temperature and then poured onto aqueous ammonium chloride solution. After extraction with ethyl acetate and evaporation a mixture of (E)- and (Z)-5-[2-(2,5-dimethoxyphenyl)ethenyl]-2-hydroxybenzoic acid methyl ester is obtained, which may be subjected to silica gel chromatography (n-hexane/ethyl acetate 9:1). The first fraction consists of the Z-isomer (colorless crystals; M.P. 78°–80°), followed by the E-isomer (colorless crystals, M.P. 80°–82°).

EXAMPLE 2

5-[2-(2,5-Dimethoxyphenyl)ethyl]-2-hydroxybenzoic acid ethyl ester

[Formula I: $R_1$, $R_2$=OCH$_3$; $R_3$=H; $R_4$=OCH$_2$CH$_3$]
[Process Variant b)]

250 mg of 5-[2-(2,5-dimethoxyphenyl)ethyl]-2-hydroxybenzoic acid or 250 mg of 5-[2-(2,5-dimethoxyphenyl)ethyl]-2-hydroxybenzoic acid methyl ester are dissolved in 10 ml of dry ethanol and treated with 0.2 ml of concentrated sulfuric acid. The mixture is refluxed for 48 hours and poured onto 150 ml of water. Following extraction with ethyl acetate and purification by chromatography on silicagel the title compound is obtained [colorless oil]:

NMR: 10.69 (s, 1H); 7.67 (d, J=2.2Hz, 1H); 7.29 (dd, J=2.2+8.5Hz, 1H); 6.91 (d, J=8.5Hz, 1H); 6.66–6.83 (m, 3H); 4.42 (qua, J=7Hz, 2H); 3.79 (s, 3H); 3.75 (s, 3H); 2.76–2.92 (m, 4H); 1.44 (tr, J=7Hz, 3H).

EXAMPLE 3

5-[2-(2,5-Dimethoxyphenyl)ethyl]-2-acetoxybenzoic acid methyl ester

[Formula I: $R_1$, $R_2$, $R_4$=OCH$_3$; $R_3$=COCH$_3$]
[Process Variant b)]

150 mg of 5-[2-(2,5-dimethoxyphenyl)ethyl]-2-hydroxybenzoic acid methyl ester (compound of Example 1) are dissolved in 2.5 ml of acetic anhydride and treated with 45 mg of pyridine. The mixture is stirred overnight at room temperature, poured onto 100 ml of water and extracted with ethyl acetate. The combined organic extracts are washed successively with aqueous 0.1N HCl, aqueous sodium bicarbonate solution and water. Following evaporation of the solvent the title compound is obtained (colorless oil):

NMR: 7.85 (d, J=2Hz, 1H); 7.34 (dd, J=2+8Hz, 1H); 6.99 (d, J=8Hz, 1H); 6.66–6.80 (m, 3H); 3.87 (s, 3H); 3.76 (s, 3H); 2.89 (s, 4H); 2.34 (s, 3H).

The following compounds of the invention (formula I) are obtained in analogous manner:

| Example No. | $R_1$ | $R_2$ | $R_3$ | $R_4$ | Process variant | M.P. or NMR |
|---|---|---|---|---|---|---|
| 4 | OCH$_3$ | OCH$_3$ | COCH$_3$ | OCH$_3$ | a)[3] | oil; NMR[1] |
| 5 | OCH$_3$ | OCH$_3$ | H | OCH$_2$CH$_2$CH$_3$ | a) b)[2] | oil; NMR[6] |
| 6 | OCH$_3$ | OCH$_3$ | H | OCH$_2$CH$_2$CH$_2$CH$_3$ | a) b)[2] | oil; NMR[7] |
| 7 | OCH$_2$CH$_3$ | OCH$_2$CH$_3$ | H | OCH$_3$ | a)[4] b) | oil; NMR[8] |

-continued

The following compounds of the invention (formula I) are obtained in analogous manner:

| Example No. | $R_1$ | $R_2$ | $R_3$ | $R_4$ | Process variant | M.P. or NMR |
|---|---|---|---|---|---|---|
| 8 | $OCH_3$ | $OCH_3$ | H | $OCH(CH_3)_2$ | a) b)[2] | oil; NMR[5] |

[1] See Example 3;
[2] Esterification starting from the corresponding compound of formula III wherein $R_5$ is hydroxy (M.P. 120–125°) prepared analogously to Example 1;
[3] Starting from the corresponding compounds of formula II wherein —X—X— is vinylene (M.P. 86–88°, E-isomer; M.P. 63–66°, Z-isomer) prepared as described in Example 1;
[4] Starting from the E/Z mixture (about 1.3:1) of the corresponding compounds of formula II wherein —X—X— is vinylene (M.P. 45–50°) prepared as described in Example 1;
[5] 10.73(s, 1H); 7.62(d, J=2.3Hz, 1H); 7.28(dd, J=2.3+8.5Hz, 1H); 6.9(d, J=8.5Hz, 1H); 6.8(d, J=9Hz, 1H); 6.66–6.75(m, 2H); 5.29(sept, J=6.25Hz, 1H); 3.79(s, 3H); 3.75(s, 3H); 2.75–2.9(m, 4H); 1.41(d, J=6.25Hz, 6H);
[6] 10.69(s, 1H); 7.65(d, J=2.2Hz, 1H); 7.29(dd, J=2.2+8.5Hz, 1H); 6.91(d, J=8.5Hz, 1H); 6.66–6.83(m, 3H); 4.32(tr, J=7Hz, 2H); 3.79(s, 3H); 3.75 (s, 3H); 2.77–2.93(m, 4H); 1.83(sex, J=7Hz, 2H); 1.06(tr, J=7Hz, 3H);
[7] 10.69(s, 1H); 7.63(d, J=2.2Hz, 1H); 7.28(dd, J=2.2+8.5Hz, 1H); 6.9(d, J=8.5Hz, 1H); 6.79(d, J=8.5Hz, 1H); 6.65–6.75(m, 2H); 4.36(tr, J=6.7Hz, 2H); 3.78(s, 3H); 3.74(s, 3H); 2.76–2.92(m, 4H); 1.70–1.85(m, 2H); 1.40–1.56(m, 2H); 1.00(tr, J=7.3Hz, 3H);
[8] 10.59(s, 1H); 7.68(d, J=2.3Hz, 1H); 7.29(dd, J=2.3+8.5Hz, 1H); 6.92(d, J=8.5Hz, 1H); 6.65–6.81(m, 3H); 3.99(qua, J=7Hz, 2H); 3.96(s, 3H); 3.94(qua, J=7Hz, 2H); 2.76-2.93(m, 4H); 1.42(tr, J=7Hz, 3H); 1.38(tr, J=7Hz, 3H).

The compounds of formula I in free form or, where such forms exist, in pharmaceutically acceptable salt form possess advantageous chemotherapeutic properties. They are useful as pharmaceuticals.

In particular, they possess antihyperproliferative/antiinflammatory and anticancer activity. The following abbreviations are used hereinafter:
CHO-K1=the cell line known as "Chinese hamster-ovary-K1"
DMEM=Dulbecco's modified eagle medium (Gibco)
EGF=epidermal growth factor
FCS=fetal calf serum
HaCaT=the cell line known as "human adult calcium temperature"
RPMI-1640=Roswell Park Memorial Institute medium 1640
TGFα=transforming growth factor α

Antihyperproliferative/antiinflammatory activity and/or anticancer activity may e.g. be determined as follows:
1. Inhibition of Proliferation in Human Keratinocyte Cell Line HaCaT (or Reference Cell Line CHO-K1):

HaCaT cells, a spontaneously transformed, TGF-α- and EGF-receptor positive non-tumorigenic human keratinocyte cell line with highly preserved phenotypic differentiation characteristics of normal keratinocytes (Boukamp et al., *J. Cell. Biol.* 106, 761–771 [1988]), are cultivated in DMEM medium supplemented with 2.2 g/l $NaHCO_3$, 0.11 g/l sodium pyruvate, 15 mM Hepes, 5% FCS, penicillin (100 U/ml), streptomycin (100 μg/ml), and glutamine (to increase the final concentration by 4 mM). CHO-K1 cells are cultured in the above medium plus 40 μg/ml proline. For the proliferation assay, cells are detached by trypsinization, suspended in fresh medium, and seeded into 96-well microtiter plates at 2000–4000 cells/0.2 ml/well. After 24 hours the medium is replaced with fresh medium containing graded concentrations of test compound. After 3–4 days of incubation, the extent of cellular proliferation is measured by a colorimetric assay using sulforhodamine B (Skehan et al., *J. Natl. Cancer Inst.* 82, 1107–1112 [1990]). The results represent the average ±standard deviation of three measurements.

In the above assay the compounds inhibit HaCaT cell proliferation with $IC_{50}$-values ranging from about 0.03 μM to about 3 μM.

Anticancer activity may e.g. be determined as follows:
2. Inhibition of Tumor Cell Proliferation:

Tumor cell lines, e.g. K-562, L1210, HeLa, SK-BR-3, MDAMB-468, MCF-7 or MDAMB-231 (all available from the American Type Culture Collection, Rockville, Md. 20852, USA), are grown in RPMI-1640 medium supplemented with 10% heat-inactivated (56° C./30 min) FCS and antibiotics (1×GIBCO penicillin-streptomycin solution). When exponential growth for tumor cell lines growing in suspension (K-562 and L1210) or 60–90% confluence for adherent cell lines (HeLa, SK-BR-3, MDAMB-468, MCF-7 and MDAMB-231) is reached, cells are harvested (adherent cells are trypsinized), suspended in fresh growth medium and seeded into 96 well culture plates at concentrations ranging between 1000 and 5000 cells/well. Cells are grown for 2–4 days in a final volume of 0.2 ml/well, at 37° C. in a humidified incubator equilibrated with 5% $CO_2$, in the presence of graded concentrations of test compound. The extent of cellular proliferation is measured by a colorimetric assay using MTT (Alley et al., *Cancer Res.* 48 [1988] 589–601) for cells growing in suspension or by sulforhodamine B for adherent cells.

In the above assay the compounds inhibit proliferation of the four cell lines mentioned above with $IC_{50}$ values ranging between about 0.019 μM and about 3 μM.

3. Effect on the Growth of Human Tumors Xenotransplanted in Nude Mice:

MiaPaCa-2 is a human pancreatic tumor cell line; the A431 cell line is derived from a human epidermoid carcinoma of the vulva. They are both available from ATCC (American Type Culture Collection). The cell cultures are grown without antibiotics and anti-fungal agents. Female Balb/C nude mice, weighing 20 to 23 g are kept as groups of 5 animals, with free access to drinking water and a pathogen-free rodent diet. The tumors are initiated from cultured tumor cell lines by injecting $10^7$ cells subcutaneously into nude mice. Once the tumors have reached approximately 1 cm in diameter, they are excised, cut into small pieces of approximately 4 by 3 mm and transplanted subcutaneously in both flanks of nude mice. One and two weeks subsequent to transplantation, the size of the tumors is determined by use of a caliber. Animals with growing tumors are randomized into control and treatment groups with identical mean tumor burden per mouse. The test compounds are given perorally. The same drug solution is used for two subsequent treatment courses. Control animals are treated with the vehicle only. At weekly intervals, tumor volumes are determined and expressed as mean tumor volume per animal ($mm^3$). Data are evaluated by use of the statistics program of RS/1 (BBN Software Products Corp.), and tests including Student's t-test and the Mann-Whitney test are applied.

In the above assay the compounds administered at a dosage of from 30 mg/kg to 100 mg/kg p.o. or from 3 mg/kg to 10 mg/kg i.v. inhibit the growth of A431 tumors (human epidermoid tumors overexpressing the EGF receptor) significantly (P<0.05 or <0.01) over the total treatment period. At the end of the experiment (4 weeks), the tumor volume of drug-treated mice is from about 10% to about 50% of that of control animals. The growth of MiaPaCa tumors (human pancreatic tumors expressing normal amounts of EGF receptor) is similarly inhibited: after 3 weeks of treatment the volume of tumors in treated mice is significantly inhibited over that of control animals.

Antihyperproliferative/antiinflammatory activity upon topical application may e.g. be determined as follows:

4. Inhibition of Oxazolone-induced Allergic Contact Dermatitis in the Mouse

Sensitization is induced by a single application of 2% oxazolone (10 μl) onto the abdominal skin of mice (8 animals per group). Hypersensitivity reaction causing pinnal swelling is elicited by a second exposure to 2% oxazolone applied to one pinna of each animal after 8 days.

Inhibition of pinnal swelling is achieved by two topical applications of test compound (30 minutes before and after elicitation of the challenge reaction). Efficacy is determined by the difference of pinnal weights of animals treated with the drug and with the vehicle (propyleneglycol/acetone 7:3), respectively, and expressed in % of swelling with vehicle application alone.

In the above assay from about 20% to about 60% inhibition is obtained at a dosage of 1.2% of test compound.

The compounds of formula I in free form or, where such forms exist, in pharmaceutically acceptable salt form are therefore useful as antiproliferative/antiinflammatory and anticancer agents in the treatment of hyperproliferative/inflammatory disorders and cancer such as in suppression of neoplastic diseases, e.g. inflammatory/hyperproliferative skin diseases, skin cancer, and cutaneous and systemic manifestations of immunologically-mediated illnesses and autoimmune diseases, such as: psoriasis, atopical dermatitis, contact dermatitis and related eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and Alopecia areata.

For these uses the dosage to be used will vary, of course, depending e.g. on the particular compound employed, the mode of administration and the treatment desired. However, in general, satisfactory results are obtained when the compounds are administered at a daily dosage of from about 0.1 mg/kg to about 10 mg/kg animal body weight intravenously, or from about 0.5 mg/kg to about 100 mg/kg p.o., suitably given in divided doses two to four times daily. For most large mammals the total daily dosage is from about 7 mg to about 2000 mg, conveniently administered, for example, in divided doses up to four times a day or in retard form. Unit dosage forms comprise, for example, from about 1.75 mg to about 1000 mg of the compounds in admixture with at least one solid or liquid pharmaceutically acceptable carrier or diluent.

The compounds may be administered in similar manner to known standards for use in such indications. The compounds may be admixed with conventional chemotherapeutically acceptable carriers and diluents and, optionally, further excipients, and administered e.g. orally in such forms as tablets and capsules.

The compounds may alternatively be administered topically in such conventional forms as ointments or creams, parenterally or intravenously. The concentrations of the active substance will, of course, vary depending e.g. on the compound employed, the treatment desired and the nature of the form. In general, however, satisfactory results are obtained e.g. in topical application forms at concentrations of from about 0.05 to about 5%, particularly from about 0.1 to about 1% by weight.

Pharmaceutical compositions comprising a compound of formula I in free form or, where such forms exist, in pharmaceutically acceptable salt form together with at least one pharmaceutically acceptable carrier or diluent also form part of the invention.

The invention further comprises a method of treatment of hyperproliferative/inflammatory disorders and cancer which comprises administering a therapeutically effective amount of a compound of formula I in free form or, where such forms exist, in pharmaceutically acceptable salt form to a patient in need of such treatment.

The compound of Example 1, i.e. 5-[2-(2,5-dimethoxyphenyl)ethyl] -2-hydroxybenzoic acid methyl ester, is the preferred compound. It has, for example, been determined that in the above assay 1 this compound has an $IC_{50}$ of 0.045 μM whereas, in contrast, the EGF receptor negative cell line CHO-K1 is inhibited with an $IC_{50}$ greater than about 0.3 μM.

In the above assay 2, this compound inhibits three out of four mammary tumor cell lines tested, namely SK-BR-3, MDAMB-468 and MCF-7 cells with an $IC_{50}$ ranging from 20 to 50 nM, whereas the mammary tumor cells MDAMB-231 and the non-mammary tumor cells K-562, L1210 and HeLa are inhibited with an $IC_{50}$ ranging from 200 to 470 nM, indicative of a selectivity for some mammary tumors, whereas colchicine unselectively inhibits all tumor cells tested with an $IC_{50}$ ranging between 5 and 20 nM.

In the above assay 3, with A431 tumors, at a dose of 30 mg/kg p.o. given 3 times a week the tumor volume of drug-treated mice is only 56.3% of that of control animals at the end of the experiment (4 weeks) and at a dose of 3 mg/kg i.v. about 40% of that of control animals. With MiaPaCa pancreatic tumors, mice treated with 30 mg/kg p.o. of compound of Example 1 over 2 weeks had a tumor size of about 46% of that of control animals; in a similar experiment inhibition with cisplatin given at a standard, comparable dosage of 10 mg/kg i.p. every third day (cisplatin normally cannot be given p.o.) reached significance only after 4 weeks of treatment (tumor size about 40% of that of control animals), even though the mean tumor volume at the start of cisplatin treatment was only approximately half of that in the treatment with compound of Example 1.

In the above assay 4, the compound of Example 1 elicits 49% inhibition of swelling at a concentration of 1.2%.

It is, therefore, indicated that for the above anticancer use the compound of Example 1 may be administered to larger mammals, for example humans, by similar modes of administration at similar dosages that conventionally employed with cisplatin. This strong anti-tumor activity is observed at dosages not suppressive of immune response and hematopoiesis, and tumor cells expressing the multidrug resistance phenotype are as sensitive to the compound as to their parental counterparts.

We claim:
1. A compound of formula I

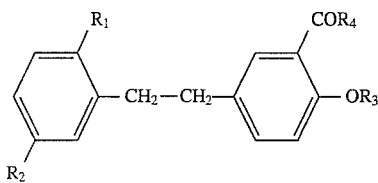

wherein
$R_1$ and $R_2$ independently are alkoxy,
$R_3$ is hydrogen or acyl, and
$R_4$ is alkoxy,
in free form or, where such forms exist, in salt form.

2. A compound according to claim 1 of formula I wherein $R_1$ and $R_2$ independently are alkoxy of 1 to 4 carbon atoms and $R_3$ and $R_4$ are as defined in claim 1.

3. A compound according to claim 1 of formula I wherein $R_1$ and $R_2$ independently are alkoxy of 1 to 4 carbon atoms, $R_3$ is hydrogen or alkylcarbonyl of altogether 2 to 5 carbon atoms, and $R_4$ is alkoxy of 1 to 4 carbon atoms.

4. The compound according to claim 1 which is 5-[2-(2, 5-dimethoxyphenyl)ethyl] -2-hydroxybenzoic acid methyl ester.

5. A compound according to claim 1 wherein either $R_1$ and $R_2$ are methoxy and $R_3$ and $R_4$ respectively are
either H and $OCH_2CH_3$,
or $COCH_3$ and $OCH_3$,
or H and $OCH_2CH_2CH_3$,
or H and $OCH_2CH_2CH_2CH_3$,
or H and $OCH(CH_3)_2$,
or $R_1$ and $R_2$ are $OCH_2CH_3$, $R_3$ is H and $R_4$ is $OCH_3$.

6. A process for the preparation of a compound according to claim 1 which comprises
a) reducing a corresponding compound of formula II

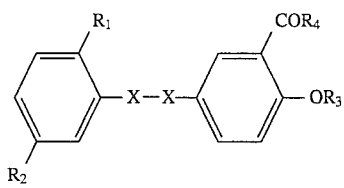

wherein —X—X— is vinylene or ethynylene, or
b) esterifying or acylating a compound of formula III

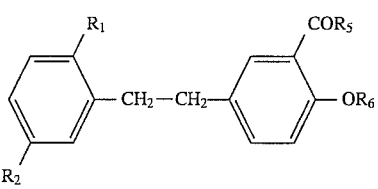

wherein
$R_1$, $R_2$, $R_3$ and $R_4$ are as defined in claim 1,
$R_5$ is hydroxy or alkoxy and
$R_6$ is hydrogen or acyl,
and optionally converting by transesterification an alkoxy group $R_4$ into a different alkoxy group $R_4$,
whereby functional groups may be in protected form and the protecting groups removed after reaction has taken place, and recovering the resultant compound of formula I in free form or, where such forms exist, in salt form.

7. A pharmaceutical composition comprising a pharmaceutically acceptable carrier or diluent and a therapeutically effective amount of a compound of claim 1 in free form or, where such forms exist, in pharmaceutically acceptable salt form.

8. A method of treating hyperproliferative or inflammatory disorders or inhibiting tumors comprising administering to a subject in need of such treatment a therapeutically effective amount of a compound of claim 1 in free form or, where such forms exist, a pharmaceutically acceptable salt form.

* * * * *